(12) United States Patent
Rahman et al.

(10) Patent No.: US 8,920,558 B2
(45) Date of Patent: Dec. 30, 2014

(54) **METHOD FOR CRYSTALLIZING *GEOBACILLUS* STRAIN T1 POLYPEPTIDE**

(75) Inventors: Raja Noor Zaliha Raja. Abd. Rahman, Selangor (MY); Abu Bakar Salleh, Selangor (MY); Mahiran Basri, Selangor (MY); Adam Leow Thean Chor, Selangor (MY)

(73) Assignee: Universiti Putra Malaysia, Serdang, Sleangor (MY)

( * ) Notice: Subject to any disclaimer, the term of this patent is extended or adjusted under 35 U.S.C. 154(b) by 842 days.

(21) Appl. No.: 12/415,437

(22) Filed: Mar. 31, 2009

(65) Prior Publication Data

US 2010/0144011 A1 Jun. 10, 2010

(30) Foreign Application Priority Data

Dec. 10, 2008 (MY) ................ PI 2008 4994

(51) Int. Cl.
*C30B 7/00* (2006.01)
*C12N 9/20* (2006.01)

(52) U.S. Cl.
CPC ............. *C12N 9/20* (2013.01); *C07K 2299/00* (2013.01)
USPC ........................................ 117/68

(58) Field of Classification Search
None
See application file for complete search history.

(56) References Cited

U.S. PATENT DOCUMENTS

| | | | | |
|---|---|---|---|---|
| 6,447,726 | B1 * | 9/2002 | Delucas et al. | 422/552 |
| 8,298,334 | B2 * | 10/2012 | Raja Abdul Rahman et al. | 117/68 |
| 2003/0219887 | A1 * | 11/2003 | Corbett et al. | 435/194 |
| 2004/0018560 | A1 * | 1/2004 | Bledsoe et al. | 435/7.1 |
| 2008/0201123 | A1 * | 8/2008 | Cosgrove | 703/11 |

FOREIGN PATENT DOCUMENTS

WO WO 2007148958 A1 * 12/2007

OTHER PUBLICATIONS

Leow et al., Crytsal Growth and Design 7:406-410, 2007.*
Matsumura et al., Proteins 70:592-598, 2007.*
Kundrot et al., Crystal Growth and Design 1:87-99, 2001.*
Amersham Protein Purification Handbook, Oct. 2001, p. 59.*
Matsumura et al., Proteins 70:592-598, 2008.*
Sousa, R., Acta Cryst. D51:271-277, 1995.*

* cited by examiner

*Primary Examiner* — David J Steadman
(74) *Attorney, Agent, or Firm* — Muncy, Geissler, Olds & Lowe, P.C.

(57) ABSTRACT

A method for crystallizing a *Geobacillus* strain T1 polypeptide under gravity or microgravity conditions is provided. A purified protein to be crystallized is provided, the purified protein being either thermostable T1 lipase or thermostable F16L lipase. A protein solution is prepared, comprising the purified protein, a buffer solution having a working pH of at least 8.5, and between 3-5% glycerol. A reservoir solution is prepared, comprising 0.1M MES, 0.1M NaH2PO4, 0.1M KH2PO4, and 1 M NaCl, and having a working pH of 6.5 or 6.6. The protein and reservoir solutions are combined to obtain a protein droplet, and protein crystals are obtained from the protein droplet by hanging-drop vapor diffusion.

8 Claims, 10 Drawing Sheets

F16L Lipase 1.70Å

FIG. 7b

T1 lipase 1.35Å

FIG. 7a

METHOD FOR CRYSTALLIZING *GEOBACILLUS* STRAIN T1 POLYPEPTIDE

FIELD OF THE INVENTION

This invention relates to a method for growing crystals under microgravity conditions and, in particular, a method for growing crystals such as protein crystals under microgravity conditions. Moreover, the present invention relates to a method of producing a single crystal. More particularly, the present invention relates to a method of producing a large single crystal having a low density of crystalline defects.

BACKGROUND OF THE INVENTION

Protein crystal growth under microgravity conditions results in substantially increased crystal size and quality. The application of a microgravity environment is the subject of several ongoing investigations which aim to increase the size and internal order of protein crystals. Numerous successful applications of a microgravity environment to the growth of high quality protein crystals have been well documented. This is extremely important, since the ability to produce high quality protein crystals has been the limiting step in a number of important macromolecule structural problems. Crystallization of proteins is an important requirement in determining protein structure. Protein crystallography is used to ascertain the three-dimensional molecular structure of protein crystals. This is essential for understanding the biological functions attributed to these macromolecules. The physical shape and folding of a protein is of increasing importance to drug companies interested in rational drug design. Drug molecules are designed to fit exactly into a binding site of a macromolecule, thus blocking its function in a given disease pathway. Producing higher quality crystals results in more accurate modelling of the 3-dimensional protein structures, and consequently more efficacious drugs can be produced. This accuracy is referred to as the resolution of the structure. The larger and more perfect crystals provide the highest resolution.

Presently, the field of macromolecular crystallography is undergoing a major technological revolution which permits more efficient and difficult structure determinations. These improvements coupled with the advances in recombinant technologies are providing an increase in the number of structures determined yearly. Typically, the growth of large, high quality protein crystals using ground-based methods requires numerous crystallization surveys to identify and maximize the proper growth conditions.

With regard to making a crystal (preferably a single crystal structure), various methods have been conventionally known. For example, a melt growth method in which a melt is slowly solidified and a solution growth method in which a solution of raw materials is cooled gradually have been provided. To avoid crystalline defects or in-homogeneity in composition and make a perfect single crystal, a zero-gravity environment such as in space or orbit has been utilized. For instance, a melt or solution is cooled under a floating state without using any container, and a crystal is made. This method is called a container-less method, and it is a stable method for making a highly pure crystal because any contamination from a container can be completely avoided. A large crystal is also made because a melt of large size can be supported without any container under a zero-gravity environment. At the beginning of crystal growth experiment in space, a perfect crystal without any defect or in-homogeneity was expected to be realized on the grounds that convection due to gravity does not occur and crystal growth proceeds in a melt or solution without any influence of disturbance.

One important field of such a space experiment is the growth of protein crystals under a microgravity environment. The growth of protein crystals is an important as well as fundamental step for determining the molecular structure and for investigating the relationship between the structure and function of protein molecules. Based upon the determination of the molecular structure, proteins can be designed to have a desired function. This is one of the major goals of protein engineering.

In view of the foregoing problems, experiments in space for growing protein crystals under microgravity conditions attracts the attention of various researchers, as such a microgravity environment does not cause convection during growth of the protein crystals. Perfect crystals are difficult to achieve on Earth. Ambient gravity and turbulence disrupt crystal formation, in that terrestrial samples mix as a result of gravity-driven convective flow. Therefore a microgravity environment promotes better crystal formation, in part due to the lack of turbulence and mixing within a liquid or gaseous sample during crystal formation. Spacecraft in low Earth orbits can provide a microgravity environment that is convection- and sedimentation-free for the study and application of fluid-based systems. With the advent of the Space Shuttle, scientists have regular access to such environments and many experiments have been initiated, including those in protein crystallization. After many trials it became clear that, for several proteins, crystallization in a microgravity environment resulted in bigger and better quality crystals. The generation of perfect crystals can sometimes be the limiting factor in determining a protein's structure. By eliminating variables such as gravity, crystals are able to form more slowly and more precisely in space. Temperature can be a significant variable in biological macromolecule and small molecule crystallization. Temperature often influences nucleation and crystal growth by manipulating the solubility and supersaturation of the sample. Thus, the control of temperature during crystal production is essential for successful and reproducible crystal growth of proteins with temperature dependent solubility. An advantage is that a temperature gradient provides precise, quick, and reversible control of relative supersaturation. In addition to standard crystallization variables (such as sample concentration, reagent composition and concentration, and pH), temperature variables can increase the probability of producing crystals as well as uncover new crystallization conditions for a sample. Protein solution temperature can be used to carefully manipulate crystal nucleation and growth. This control can also be used to etch or partially dissolve and then grow back the crystal in an attempt to improve crystal size, morphology, and quality. Temperature control is noninvasive and can manipulate sample solubility and crystallization with altering reagent formulation.

SUMMARY OF THE INVENTION

The present embodiment relates to a method of crystallizing a purified protein, wherein the protein is isolated from a purified *Geobacillus* sp.strain T1. The purified protein includes thermostable T1 lipase and thermostable F16L lipase, whereby the thermostable T1 lipase and thermostable F16L lipase are obtained at a temperature of between 16° C. and 70° C. Preferably, it is understood that the T1 lipase has a working protein concentration of at least 2 mg/ml and the F16L lipase has a working protein concentration of at least 4 mg/ml.

Accordingly, it is also understood that the present invention relates to a method of crystallizing a purified protein in a gravity environment; and crystallizing a purified protein in a microgravity environment. This present method relates to the preparation of a protein solution and a reservoir solution. As a result of the method, a protein droplet is obtained. The protein droplet obtained for the T1 and FI6L lipase has a working protein insert of between 5 µl and 40 µl, whereby the insert includes a protein concentration of at least 1.25 µl and a reservoir solution of at least 1.25 µl. The protein concentration is preferably between 1.25 µl and 10 µl, and the reservoir solution is preferably between 1.25 µl and 10 µl. Moreover, the protein solution includes T1 lipase or F16L lipase, and a buffer solution having a working pH of at least pH 8.5 and between 3% and 5% glycerol.

Yet another embodiment of the present invention relates to a method of crystallizing a purified protein (preferably a thermostable lipase T1 and/or a thermostable F16L lipase) having the means to grow in the gravity environment whereby the crystallization process has a working temperature of at least 20° C. and a working time of at least 8 days. Following to this, the crystallized thermostable T1 lipase and/or thermostable F16L lipase is obtained from *Geobacillus* sp.strain T1. It is understood that a T1 lipase having a size of at least 1.8 Å under the gravity environment and at least 1.35 Å under microgravity environment is obtained, and a F16L lipase having a size of at least 1.8 Å under gravity environment and at least 1.7 Å under microgravity environment is obtained.

DETAILED DESCRIPTION OF THE INVENTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. It must be noted that as used herein and in the appended claims, the singular forms "a," "an," and "the" include plural referents unless the context clearly dictates otherwise.

In a microgravity environment, the absence of convective heat transfer produces some undesirable results. Solution cooling and the resulting supersaturation proceed by diffusion. Solution adjacent to a cooled wall or fluid-gas interface will have a localized increase in its supersaturation. The proximity of solid surfaces or fluid-gas interfaces to the nucleated crystals tends to distort the mass diffusion fields around the crystals. This results in the nucleation of uncontrolled numbers of crystals on the surfaces, such as the walls of the container, or on the free surface of the liquid. The nucleation of large numbers of crystals at one time limits the size to which the crystals will grow by rapidly depleting the solution of solute. This is particularly troublesome in protein crystal growth where the production of large crystals using microgravity is desired. Protein crystal growth under microgravity conditions results in substantially increased crystal size and quality. The application of the microgravity environment is the subject of several ongoing investigations which aim to increase the size and internal order of protein crystals.

The object of the present invention is to develop a suitable protein crystallization process on earth and in zero-gravity. Moreover, the invention relates to preferred conditions to develop protein crystals or 3D crystal structures. Furthermore, the preferred embodiment of the present invention relates to an evaluation of 3D crystal growth under microgravity (zero-gravity) and on earth. In addition, the invention also relates to the quality of protein crystals grown on earth and in zero-gravity. The present invention provides a new and improved method for growing protein crystals and for screening crystallization conditions in solution crystal growth. As such, the principal object of the present invention, which will be described subsequently in greater detail, is to provide a new and improved method for growing protein crystals and for screening crystallization conditions in solution crystal growth which has all the advantages of the prior art and none of the disadvantages.

It is still further an object of the present invention to provide a new and improved method for growing protein crystals and for screening crystallization conditions in solution crystal growth which can be used to screen for crystal growth conditions for any variety of small-molecule crystals. It is yet another object of the present invention to provide a new and improved method for growing protein crystals under microgravity conditions and for screening crystallization conditions in solution crystal growth which greatly reduces the total manpower required for conducting experiments with the present invention.

BEST MODE TO CARRY OUT THE INVENTION

Examples:

The followings are the preferred methods used in the preparation of 3D crystal structure on ground level (earth) and under zero-gravity (space/microgravity). At least two thermostable lipases were used in the present invention. The two thermostable lipases utilized are T1 lipase (hereafter "T1") and F16L lipase (hereafter "F16L"). The T1 and F16L were optimized between 16° C. and 60° C. with an optimum working temperature of 20° C. The thermostable lipases were isolated from *Geobacillus* sp. Strain T1. The *Geobacillus* T1 (preferably known as *Geobacillus* T1 & *Geobacillus* zalihae T1) is understood to have an accession number of EMBL/GenBank/DDBJ Accession No: A7367764 and NBRC 101842 and can be obtained from the Department of Biotechnology and Molecular Sciences, University Putra Malaysia. Furthermore, the T1 and F16L have a protein concentration of between 2.5 mg/ml and 4.0 mg/ml.

The following methods are segmented into pre-flight activity, in-flight activity, and post-flight activity. The pre-flight activity includes the following: preparation of protein(s), wherein the preferred protein(s) are T1 and F16L lipase. This purification process is conducted at ground level. As a result, two purified proteins were obtained at the end of this method, i.e., purified T1 lipase and F16F lipase. Accordingly, during the in-flight activity, preparation to insert the T1 and F16L lipase into a cell barrel was conducted. At this stage, observation of the size of the protein was noted. Furthermore, during the post flight activity, verification of the size of the protein was conducted in a further experiment. A comparison of the size of the protein at ground level and micro-gravity was conducted.

Pre-Flight Activities:—Preparation of purified protein (ground).

a) Two proteins (T1 and F16L) which were successfully crystallized in the laboratory of the Department of Biotechnology and Molecular Sciences, University Putra Malaysia. An expression method followed by purification was conducted. Pure protein with a specified protein concentration was prepared and a purified T1 and F16L lipase were obtained.

b) The purified protein(s) were placed into sealed eppendorf tubes and precipitating solution(s) were kept in Universal bottles. The above were packed in a packing container under dry-ice for shipment at 0° C. (0 to −20° C., dry ice condition).

c) Crystallization of T1 lipase was conducted, whereby protein samples were centrifuged at 14,000 rpm to remove any precipitate. Using a suitable hardware, the protein was first inserted into the Cell Barrel through a top surface of a Cell Body by carefully pressing into place with a clean firm object or the ground handle. The Cell Barrel was rotated at 180° to a fill-in position in order to prepare sample loading. The precipitating solution (about 500 μl) was pipetted into the PPT Reservoir. Chromex was dropped into the precipitating solution and pressed until the surface of the Chromex was parallel with the top surface of the PPT reservoir. To ensure supersaturation, small amounts of reservoir solution were added until no more was absorbed and the PPT reservoir was placed back into the Assembly. The Access Cap was temporarily removed from the same experiment location. The desired amount of T1 lipase and the desired amount of the precipitant solution (Table 2) were pipetted into the Protein Insert with a 1:1 ratio. The principle investigator (PI) gently mixed the two solutions and placed the Access Cap back into a closed position. All of the foregoing steps were repeated until all chambers were filled. After all chambers were filled, the PI rotated the cell barrel 90°, so that the lever was aligned with the red color mark. The experiment was therefore at a deactivated position and prepared 24 hours prior to launch, and then transferred to the engineering team for a leak test and packaging preparation. At this stage and prior to launch the PCS kit must be kept at a temperature of 10 to 25° C.

d) Crystallization of F16L lipase was conducted. Protein samples were centrifuged at 14,000 rpm to remove any precipitate. Using a suitable hardware, the protein was first inserted into the Cell Barrel through a top surface of a Cell Body by carefully pressing into place with a clean firm object or the ground handle. The Cell Barrel was rotated at 180° to a fill-in position in order to prepare sample loading. The precipitating solution (about 500 μl) was pipetted into the PPT Reservoir. Chromex was dropped into the precipitating solution and pressed until the surface of the Chromex was parallel with the top surface of the PPT reservoir. To ensure supersaturation, small amounts of reservoir solution were added until no more was absorbed and the PPT Reservoir was placed back into the Assembly. The access Cap was temporarily removed from the same experiment location. The desired amount of F16L lipase and the desired amount of the precipitant solution (Table 2) were pipetted into the Protein Insert with a 1:1 ratio. The principle investigator (PI) gently mixed the two solutions and placed the Access Cap back into a closed position. All of the foregoing steps were repeated until all chambers were filled. After all chambers were filled, the PI rotated the cell barrel 90°, so that the lever was aligned with the red color mark. The experiment was therefore at a deactivated position and are prepared 24 hours prior to launch, and then transferred to the engineering team for a leak test and packaging preparation. At this stage and prior to launch the PCS kit must be kept at a temperature of 10 to 25° C.

Figure 1A:
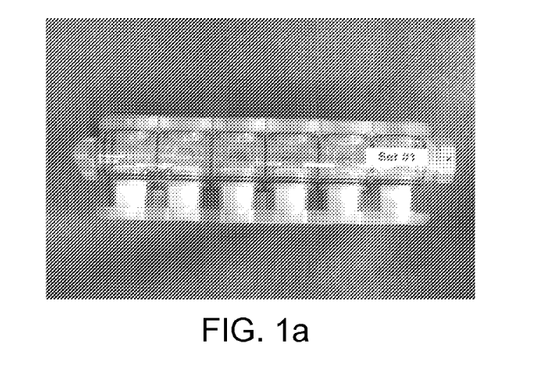
FIGS. 1a-1d represent the activation process, wherein the samples (containing purified T1 and FI6L lipase) are kept in the cell chamber
Figure 1B:
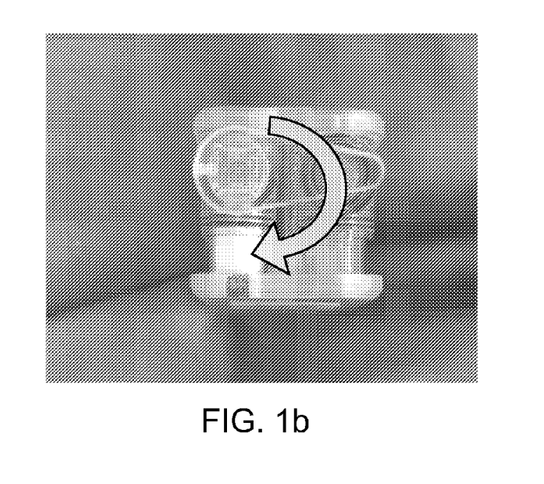
Figure 1C:
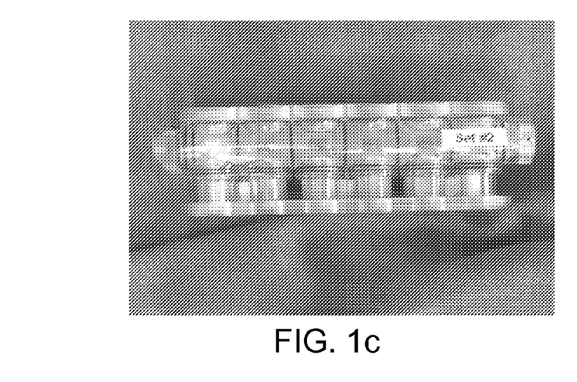
Figure 1D:
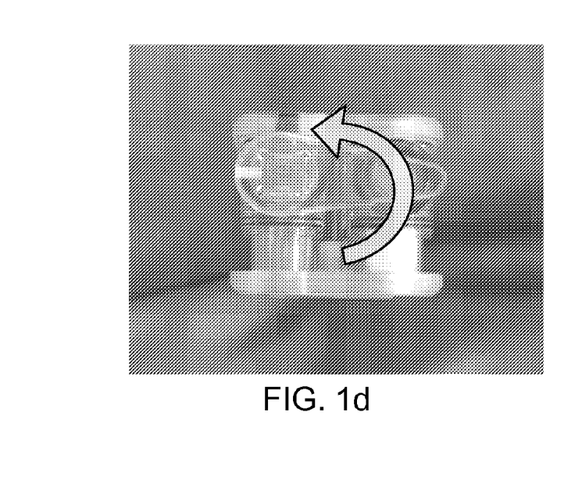

In-Flight Activities:—In the Space Station a) A space representative or preferably an astronaut will activate the crystal growth experiments by rotating the cell barrel at about 90° whereby the lever is rotated from one indication mark to another indication mark, preferably a red color mark pointing to green color mark. During this activation, the protein chamber is rotated for the purpose of its vapour contacting or sealing with the reservoir. Water molecules will migrate from the protein droplet through vapour space into a concentrated reservoir. As the volume of the protein droplet decreases, the concentration of protein increases and protein crystals are formed. As the experiment continues, this relates to the crystals growing larger.

b) After a successful launch and activation process, the hardware should be kept at an ambient temperature and stable position. It should not be disturbed except for the required daily observation and should be in correct orientation at all times.

c) Before the end of the mission, the astronaut will deactivate the experiment by rotating the chamber 90° back to its original position (i.e. re-align the lever from the green marker to the red marker) to reseal the samples before returning to Earth. The samples remain sealed until returned to the laboratory for further analysis. It is important that the crystals should remain unshaken and be in a position that ensures survivability during landing and after landing, until handed back to the PI.

d) FIGS. 1a-d represent the activation process, wherein the samples (containing purified T1 and F16L lipase) are kept in the cell chamber. In particular, FIG. 1a shows the F16L lipase samples with the lever in a deactivated position, and FIG. 1b shows the F16L lipase samples with an arrow indicating the movement of the lever 90° clockwise to an activated position, wherein the free end of the lever is aligned with an activation mark. FIG. 1c shows the T1 lipase samples with the lever in a deactivated position, and FIG. 1d shows the T1 lipase samples with an arrow indicating the movement of the lever 90° counterclockwise to an activated position, wherein the free end of the lever is aligned with an activation mark.

Figure 3:
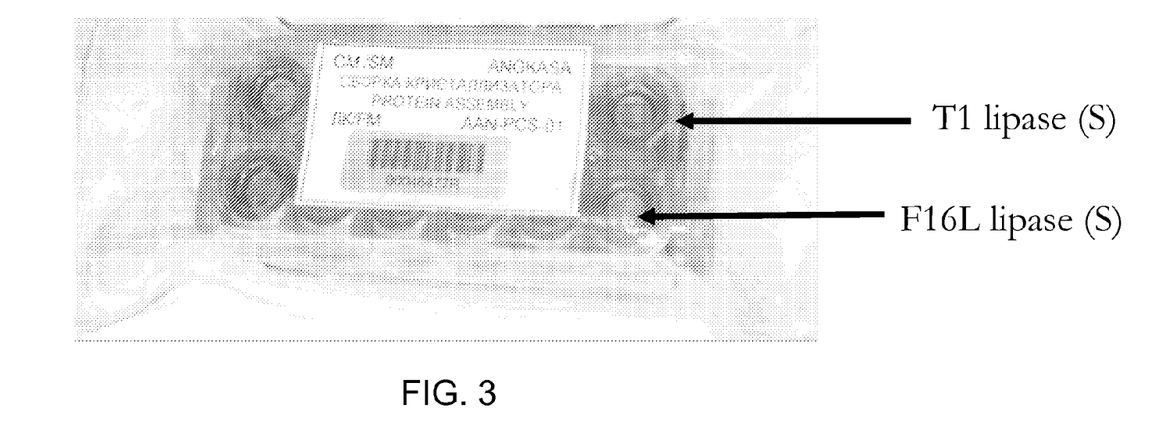
FIGS. 3 and 4 represent the samples in space and on the ground (earth), respectively.
Figure 4:
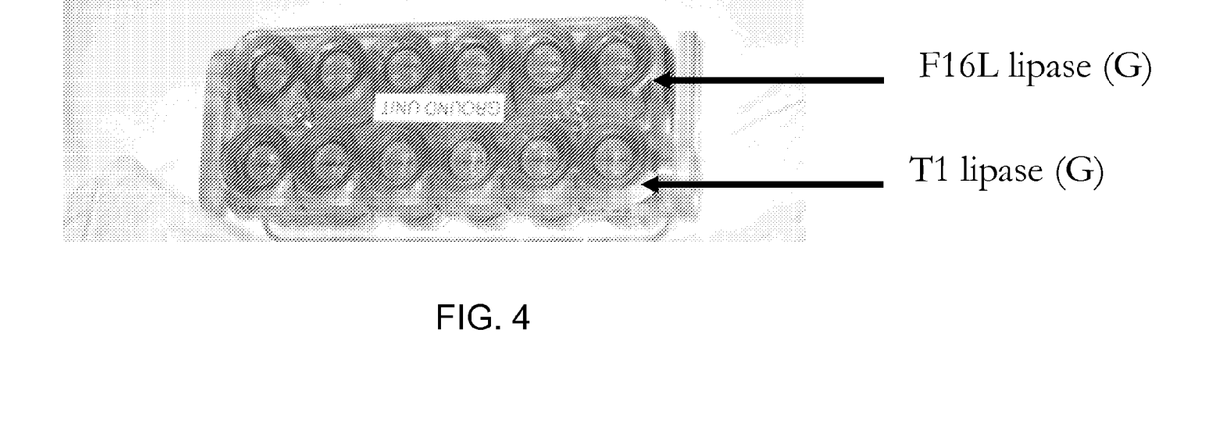

Post-Flight Activities:

a) At the landing site, the PCS Kit is retrieved and the samples are transported to a suitable laboratory for further analysis, wherein the samples are carried under an ambient temperature (10° C.-25° C.).

b) Ground based activities: A synchronous ground control activity will be conducted for the pre-flight and in-flight activities at the same time, under similar conditions. Crystal(s) formed will then be subjected to X-ray diffraction for structure determination. FIGS. 3 and 4 represents the samples in space and on the ground (earth), respectively.

c) The samples containing T1 and/or F16L lipase crystal(s) will be studied using X-ray diffraction. To facilitate successful removal of protein crystals from the cell growth assembly, the cell barrel should be in a fully activated position. The PPT reservoir will be removed from the bottom of the cell and the top of the growth cell assembly will be gently rested on a flat surface. The Protein Insert side of the ground tool will be slowly placed into the assembly and firmly pushed until the protein insert is out of the assembly and resting on the clean surface. The protein insert should now be accessible to the open environment and, using a small hair-loop or other protein crystal tool, will be gently and carefully removed from the protein insert for analysis.

d) Crystallization holds the molecules still so that the researchers can aim a single-electron X-ray beam at them. The electrons refract off the electrons of a molecule and create a pattern of dots on an X-ray film or digital camera chip. The pattern can then be converted to a density map that is the same general shape as the molecule. The expected high quality crystals to be crystallized in space may contribute significantly to the increase in diffraction data necessary to obtain higher spectral resolutions for better structural information. With this structural information, the PI can determine how the protein functions and can design new enzymes that target specific function(s).

Figure 2A:
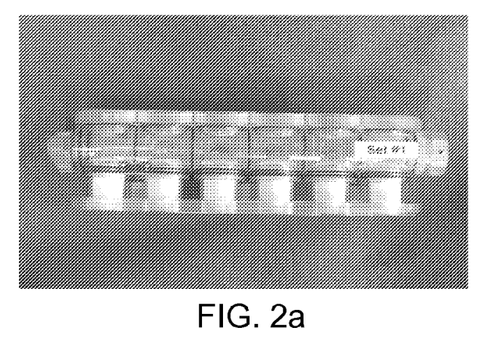
FIGS. 2a-2d represent the deactivation process, wherein the samples (containing purified T1 and F16L lipase) are removed from the cell chamber.
Figure 2B:
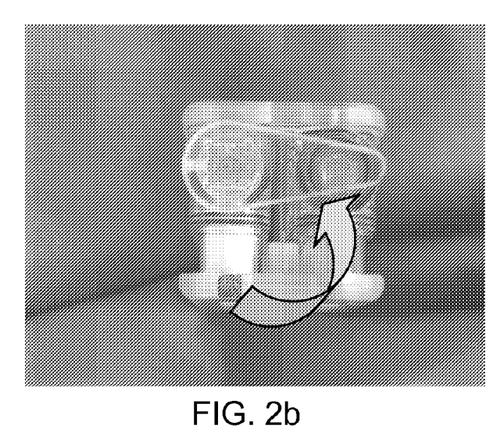
Figure 2C:
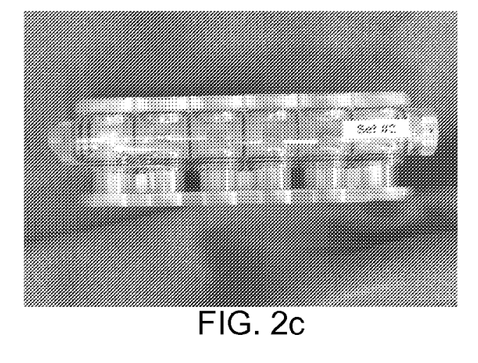
Figure 2D:
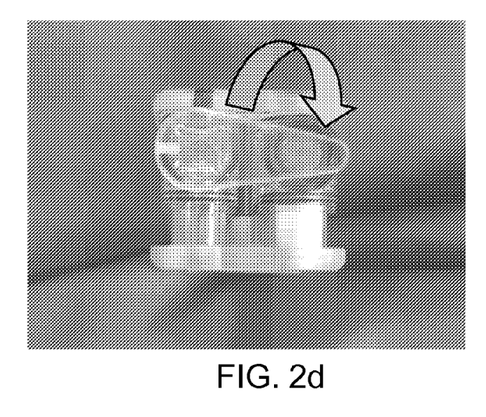

FIGS. 2a-d represent the deactivation process, wherein the samples (containing purified T1 and F16L lipase) are removed from the cell chamber. In particular, FIG. 2a shows the F16L lipase samples and FIG. 2b shows the F16L lipase samples with an arrow indicating the movement of the lever 90° counterclockwise to a de-activated position, wherein the free end of the lever is aligned with a deactivation mark. FIG. 2c shows the T1 lipase samples, and FIG. 2d shows the T1 lipase samples with an arrow indicating the movement of the lever 90° clockwise to a deactivation position, wherein the free end of the lever is aligned with a deactivation mark.

Preferred Equipment Used to Carry Out the Present Embodiment.

Equipment Description

The PCS experiment requires the following equipment:

A payload, provided by the PI, composed of:

i. PCS Kit (AAN-PCS-0).

The kit consists of one (1) Protein Assembly (AAN-PCS-01), one (1) HOBO Temperature Data Recorder (AAN-PCS-02) and one (1) Nomex Bag (AAN-PCS-03).

a. One (1) Protein Assembly (AAN-PCS-01).

The Protein Assembly has two (2) sets of High Density Protein Crystal Growth (HDPCG) apparatus. The first set of the HDPCG apparatus contains thermostable F16L Lipase, and the label shall be Set#1. The second set of the HDPCG apparatus contains thermostable T1 Lipase, and the label shall be Set#2. Each of the HDPCG apparatus has its own activation/deactivation handle or lever.

This experiment will be conducted using crystallization chambers developed by the University of Alabama and Bioserve USA. The Protein Assembly has two (2) sets of HDPCG apparatus that have been combined into a single and manually-operated device. The HDPCG apparatus is a vapour-diffusion device and has six (6) experiment chambers. Each chamber contains protein solution and precipitating (or crystallizing) agent. The HDPCG apparatus comes with 3-levels of containment with sealed containers constructed of Zeonor (Cyclo Olefin Polymers, low offgas, high chemical resistance), clear polycarbonate, and triple O-rings in sealed interfaces and stainless screws, and are rated/tested for vacuum exposure.

The Protein Assembly is contained in one (1) heat-sealed Teflon PTFE-film bag as an outer ($4^{th}$) level of containment. These materials are rated for, and compatible with, high humidity, high oxygen environments and can be vacuum-exposed at the published depressurization and repressurization rates and ambient pressures. The list of the protein specimen and its associated precipitating agent are as shown in Table 1 below:

TABLE 1

Protein specimen and its associated precipitating agent

| | Protein Sample: | Precipitant Solution: |
|---|---|---|
| Set #1 (HDPCG) | Name: Thermostable F16L Lipase (43 kDa) Protein Concentration: 4 mg/ml Volume: 5 ml | Name: 0.1M $NaH_2PO_4$ 0.1M $KH_2PO_4$ 0.1M MES pH6.5 1.0M NaCl Volume: 50 ml |
| Set #2 (HDPCG) | Name: Thermostable T1 Lipase (43 kDa) Protein Concentration: 2-4 mg/ml (3% glycerol added) Volume: 5 ml | Name: 0.1M $NaH_2PO_4$ 0.1M $KH_2PO_4$ 0.1M MES pH6.5 1.0M NaCl Volume: 50 ml | b. One (1) HOBO Temperature Data Recorder (AAN-PCS-02).

The HOBO® is an autonomous data (temperature) recorder, powered by small internal Manganese Dioxide Lithium battery (1x CR2032 each). These data recorders are routinely flown aboard the NSTS/ISS. The HOBO® data recorders were flown aboard STS-95, 93, 106, 100, 110, 112. The batteries are vacuum tested to <0.1 psi for >6 hours, inspected for leaks, and voltage is measured both unloaded and loaded prior to flight integration. Batteries will not be accessible on orbit and cannot be replaced by the crew. HOBO® data is stored in non-volatile memory and therefore, battery life does not constitute the 'operational life' of the payload. HOBO is stored inside a heat-welded ESD bag.

c. One (1) Nomex Bag (AAN-PCS-03).

The Nomex Bag is used to store the Protein Assembly and HOBO during the transport to and from the ISS-RS. This is a bag which created from a type of fiber with an extraordinary combination of high-performance heat- and flame-resistant properties, as well as superior textile characteristics.

Figure 5A:
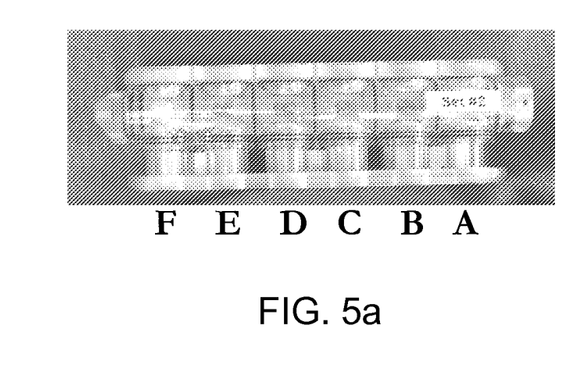
FIG. 5a shows the T1 lipase samples labeled consecutively as samples A-F, and FIGS. 5b-5c demonstrate the size of the T1 lipase crystals in each of samples A-F on the ground and in space, respectively.
Figure 5B:
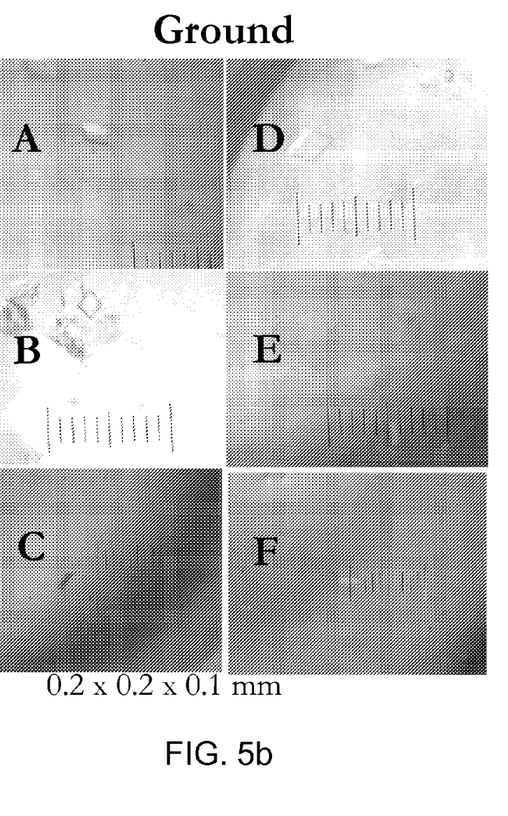
Figure 5C:
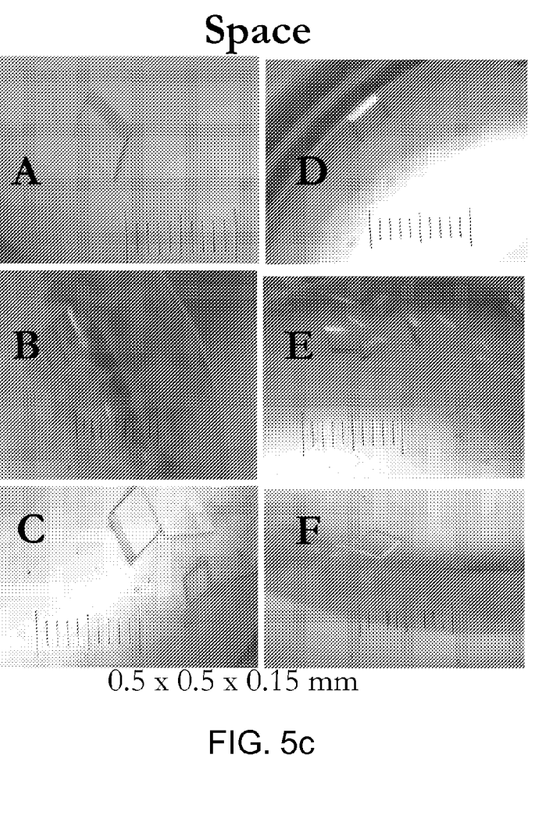
Figure 5D:
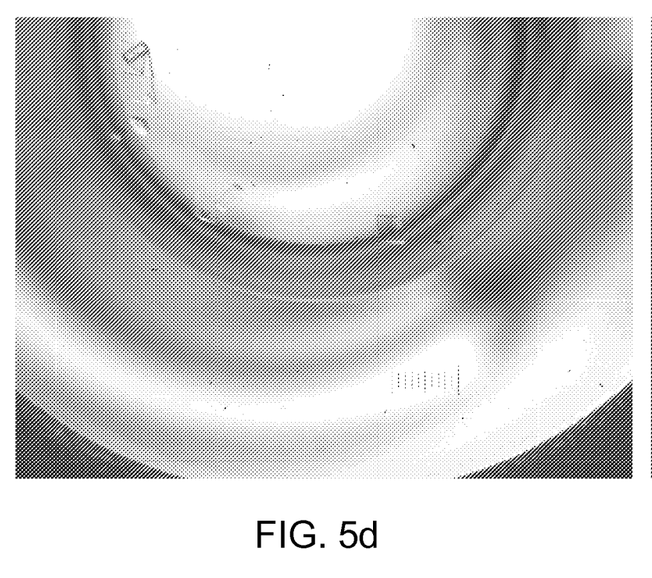
FIGS. 5d and 5e also demonstrate the size of the T1 lipase crystals in space and on the ground, respectively.
Figure 5E:
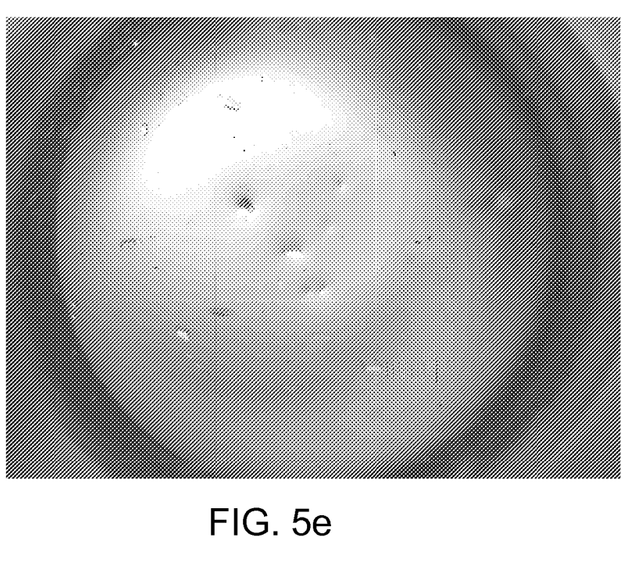
Figure 6A:
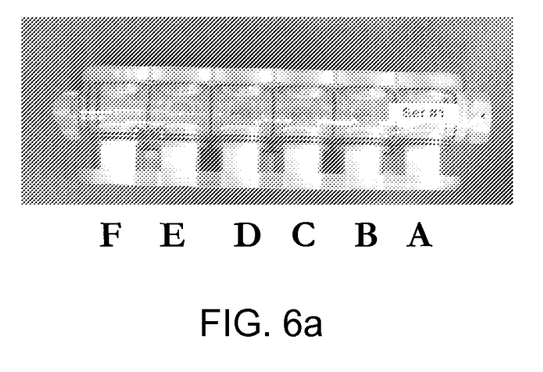
FIG. 6a shows the F16L samples labeled consecutively as samples A-F, and FIGS. 6b-6c demonstrate the size of the F16L lipase crystals in each of samples A-F from the ground and in space, respectively.
Figure 6B:
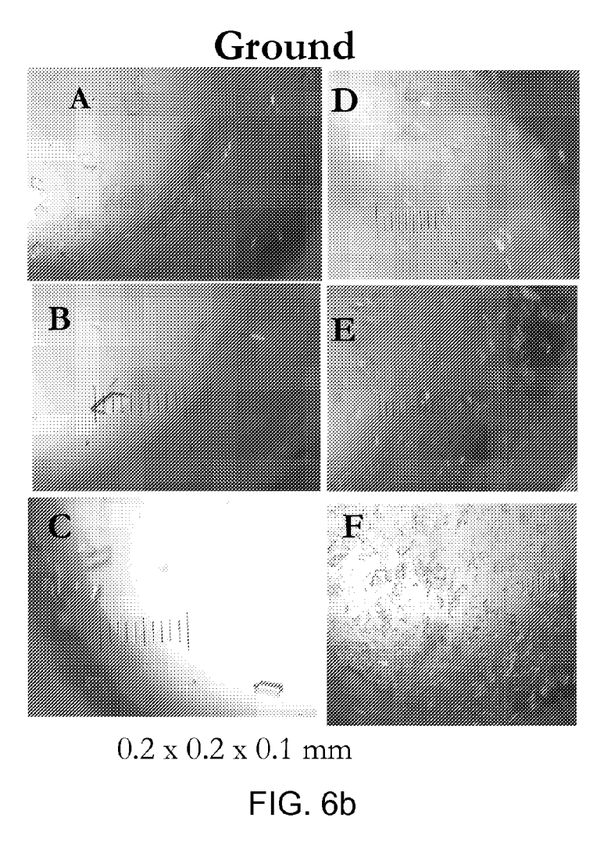
Figure 6C:
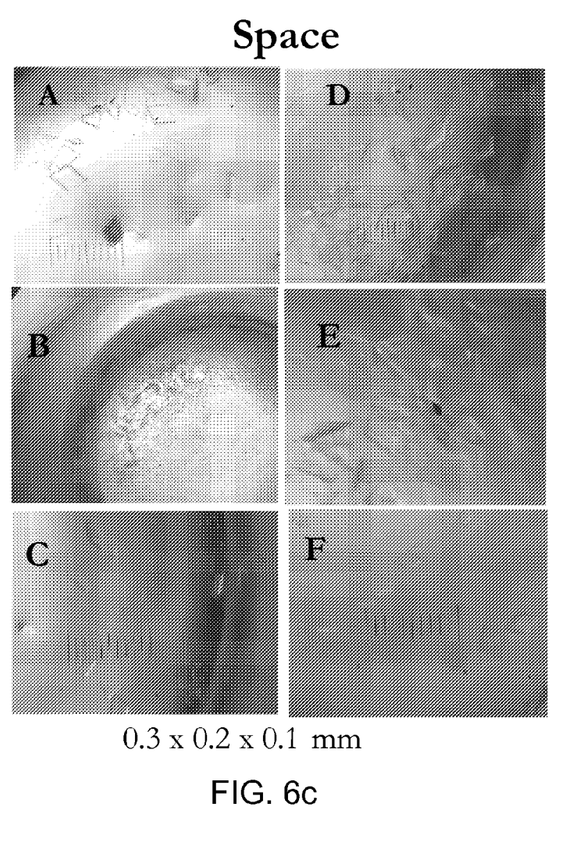
Figure 6D:
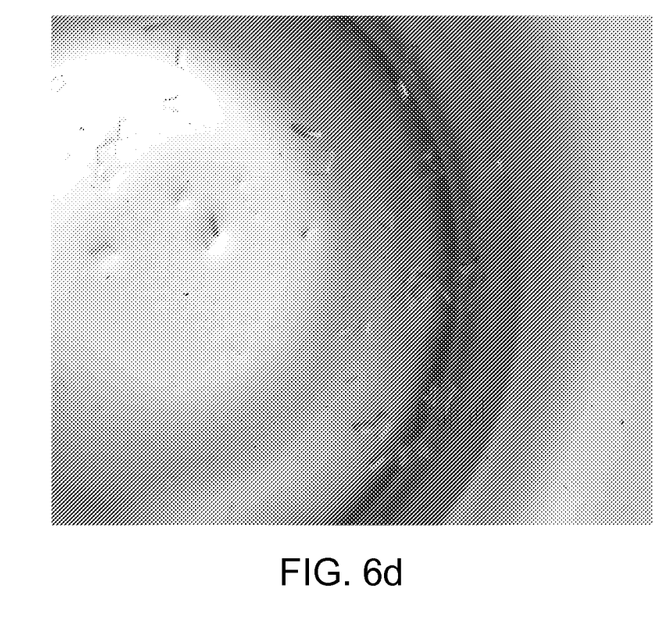
FIGS. 6d and 6e also demonstrate the size of the F16L lipase crystals in space and on the ground, respectively.
Figure 6E:
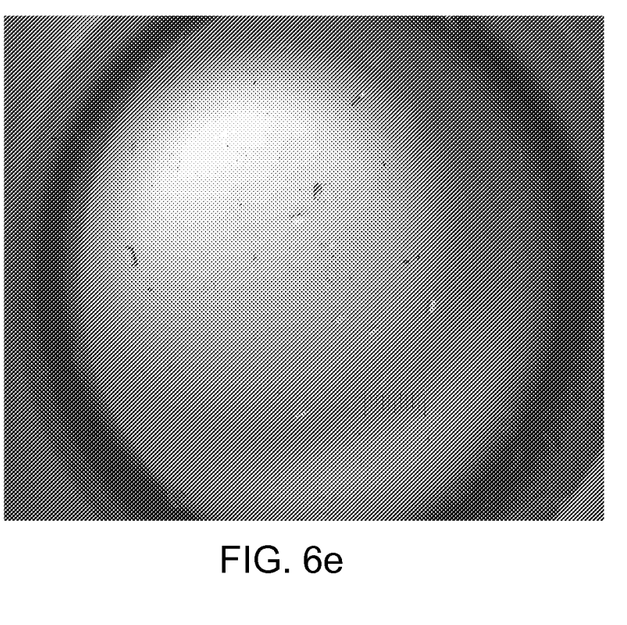
Figure 7A:
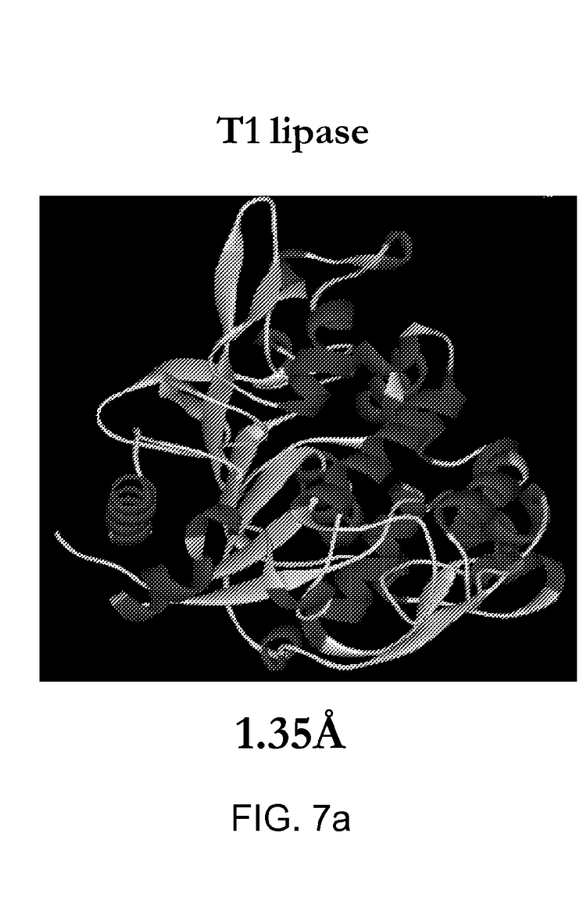
FIGS. 7a and 7b show a structure of T1 lipase and F16L lipase crystals, as grown in space.
Figure 7B:
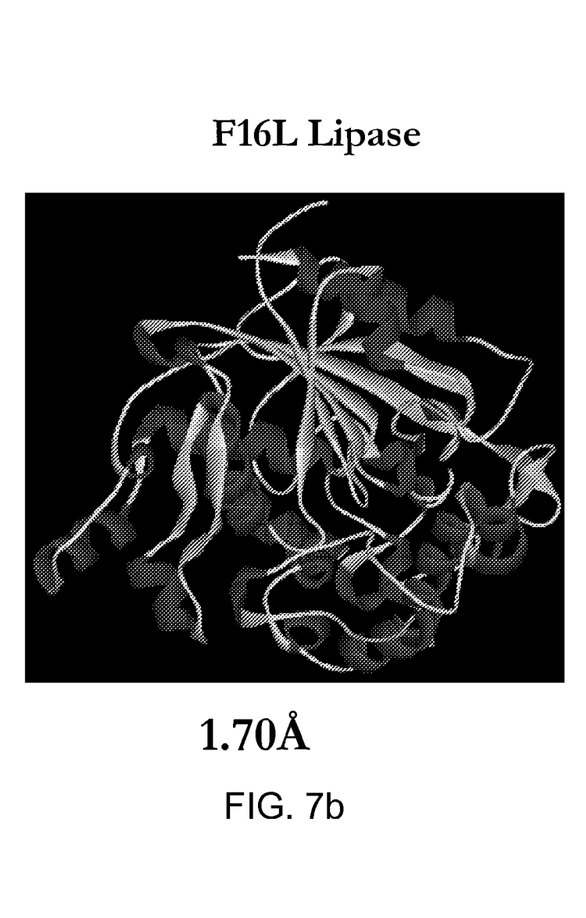

Tables 2 and 3 represent properties of the T1 lipase and F16L lipase. Table 4 represents the comparison of 3D crystal structure obtained on earth and in space. Table 4 shows the comparison of T1 and F16L lipase in space and on the ground (earth). Following this, FIGS. 5b-5c show the size of the T1 lipase crystals of samples A-F on the ground and in space, respectively. FIGS. 6b and 6c show the size of the F16L lipase crystals of samples A-F on the ground and in space, respectively. FIG. 7 shows a structure of T1 lipase and F16L lipase as crystallized in space. Table 5 represents data collected for T1 lipase in space and Table 6 represents data collected for F16L lipase in space.

TABLE 2

| T1 lipase | |
|---|---|
| Method | Hanging-drop vapor-diffusion |
| Protein solution | 2 mg/ml T1 lipase<br>50 mM Tris-HCl pH 8.5<br>3% Glycerol |
| Reservoir solution | 0.1M MES pH 6.6<br>0.1M NaH$_2$PO$_4$<br>0.1M KH$_2$PO$_4$<br>1 M NaCl |
| Droplet | 40 μl Protein insert (10 ul of protein solution, 10 μl of reservoir solution)<br>20 ul proteins insert (5 ul of protein solution, 5 μl of reservoir solution)<br>10 ul proteins insert (2.5 ul of protein solution, 2.5 μl of reservoir solution)<br>5 ul proteins insert (1.25 ul of protein solution, 1.25 μl of reservoir solution) |
| Temperature | 20° C. |
| Time | 8 days |

TABLE 3

| F16L lipase | |
|---|---|
| Method | Hanging-drop vapor-diffusion |
| Protein solution | 4 mg/ml F16L lipase<br>50 mM Tris-HCl pH 8.5 |
| Reservoir solution | 0.1M MES pH 6.6<br>0.1M NaH$_2$PO$_4$<br>0.1M KH$_2$PO$_4$<br>1 M NaCl |
| Droplet | 1) 40 μl Protein insert (10 ul of protein solution, 10 μl of reservoir solution)<br>2) 20 ul proteins insert (5 ul of protein solution, 5 μl of reservoir solution)<br>10 ul proteins insert (2.5 ul of protein solution, 2.5 μl of reservoir solution)<br>5 ul proteins insert (1.25 ul of protein solution, 1.25 μl of reservoir solution |
| Temperature | 20° C. |
| Time | 8 days |

| Crystal | Protein Concentration | Formulation | Size (mm) | Space group | Resolution (Å) |
|---|---|---|---|---|---|
| T1 Lipase Earth | 2.0 mg/L | 0.1M MES pH 6.6<br>0.1M NaH$_2$PO$_4$<br>0.1M KH$_2$PO$_4$<br>1 M NaCl<br>(3% glycerol) | 0.2 ×<br>0.2 ×<br>0.1 | C121 | 1.8 |
| Space | 2.0 mg/L | As above | 0.5 ×<br>0.5 ×<br>0.15 | C121 | 1.35 |
| F16L Lipase Earth | 4.0 mg/L | 0.1M MES pH 6.6<br>0.1M NaH$_2$PO$_4$<br>0.1M KH$_2$PO$_4$<br>1 M NaCl | 0.2 ×<br>0.2 ×<br>0.1 | C121 | 1.8 |
| Space | 4.0 mg/L | As above | 0.3 ×<br>0.2 ×<br>0.1 | C121 | 1.7 |

| | |
|---|---|
| Source | SPring-8 BL41XU |
| Crystal system | Monoclinic |
| Space group | C121 |
| Cell parameters (Å) | a = 117.39, b = 80.84,<br>c = 99.6, β = 96.46° |
| Wavelength (Å): | 0.900 |
| Resolution range (Å):<br>(outer shell) | 40.3-1.35 |
| Completeness (%) | 95.9 (92.3) |
| a/σ | 11.6 (3.9) |
| Redundancy | 2.7 (2.6) |
| † R$_{sym}$ (%) | 4.3 (33.5) |

| | |
|---|---|
| Source | SPring-8 BL41XU |
| Crystal system | Monoclinic |
| Space group | C121 |
| Cell parameters (Å) | a = 117.79, b = 81.05,<br>c = 99.6, β = 96.56° |
| Wavelength (Å): | 0.900 |
| Resolution range (Å):<br>(outer shell) | 40.3-1.7 |
| Completeness (%) | 97.6 (97.9) |
| a/σ | 15.0 (5.4) |
| Redundancy | 1.9 (1.9) |
| † R$_{sym}$ (%) | 3.8 (33.9) |

As described in detail above, the present invention permits the production of a high grade single crystal without any crystal defect or inhomogeneity in composition which has fewer slips or twins based on strains and less contamination with impurities. A large-sized single crystal can also be produced. A zero-gravity or microgravity environment such as in outer space can be utilized effectively.

The invention claimed is:

1. A method of crystallizing a purified protein, the method comprising:
providing a purified protein to be crystallized, the purified protein being thermostable T1 lipase having been isolated from *Geobacillus* sp. strain T1;
preparing a protein solution comprising the purified protein, a buffer solution having a working pH of at least 8.5, and between 3-5% glycerol, wherein the concentration of the protein is at least 2 mg/ml;
preparing a reservoir solution comprising 0.1M MES, 0.1M NaH$_2$PO$_4$, 0.1M KH$_2$PO$_4$, and 1 M NaCl, and having a working pH of 6.5 or 6.6;
combining the protein solution and the reservoir solution to obtain a protein droplet; and growing protein crystals from the protein droplet by hanging-drop vapor diffusion;

wherein said protein crystals are grown in a microgravity environment for at least eight days at a temperature of at least 20° C. using High Density Protein Crystal Growth (HDPCG) crystallization hardware.

2. The method as claimed in claim 1, wherein the volume of the protein solution and the reservoir solution is between 1.25 µl and 10 µl.

3. The method as claimed in claim 1, wherein the protein droplet has a protein insert with a volume of between 5 µl and 40 µl.

4. The method as claimed in claim 1, wherein the protein droplet is incubated at a working temperature of 20° C.

5. The method as claimed in claim 1, wherein said growing of said protein crystals produces a protein crystal having a size of at least 1.35 Å.

6. The method as claimed in claim 1, wherein said growing of said protein crystals produces a protein, crystal having a resolution size of at least 1.35 Å.

7. The method as claimed in claim 1, wherein said protein solution contains 3% glycerol.

8. The method as claimed in claim 1, wherein said reservoir solution has a pH of 6.6.

* * * * *